US008805467B2

(12) United States Patent
Yobas et al.

(10) Patent No.: US 8,805,467 B2
(45) Date of Patent: Aug. 12, 2014

(54) PROBE ELEMENT AND METHOD OF FORMING A PROBE ELEMENT

(75) Inventors: Levent Yobas, Singapore (SG); Ajay Agarwal, Singapore (SG); Ramana Murthy Badam, Singapore (SG); Rama Krishna Kotlanka, Singapore (SG); Xiang Jie Cyrus Foo, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 130 days.

(21) Appl. No.: 13/505,023

(22) PCT Filed: Oct. 29, 2010

(86) PCT No.: PCT/SG2010/000419
§ 371 (c)(1),
(2), (4) Date: Sep. 24, 2012

(87) PCT Pub. No.: WO2011/053254
PCT Pub. Date: May 5, 2011

(65) Prior Publication Data
US 2013/0012801 A1 Jan. 10, 2013

(30) Foreign Application Priority Data
Oct. 30, 2009 (SG) ................. 200907243

(51) Int. Cl.
*A61B 5/04* (2006.01)
*A61N 1/05* (2006.01)
(52) U.S. Cl.
USPC ........................ 600/377; 600/378; 607/116

(58) Field of Classification Search
CPC ............ A61B 5/04001; A61B 5/0478; A61N 1/0551; A61N 1/0534
See application file for complete search history.

(56) References Cited

U.S. PATENT DOCUMENTS

| 4,628,944 | A | 12/1986 | MacGregor et al. |
| 5,928,207 | A | 7/1999 | Pisano et al. |
| 6,187,210 | B1 | 2/2001 | Lebouitz et al. |
| 6,973,342 | B1 | 12/2005 | Swanson |
| 7,548,775 | B2 | 6/2009 | Kipke et al. |
| 8,263,986 | B2 * | 9/2012 | Hajj-Hassan et al. .......... 257/84 |
| 2006/0265039 | A1 | 11/2006 | Bartic et al. |

FOREIGN PATENT DOCUMENTS

| WO | WO9964580 A1 | 12/1999 |
| WO | WO2007089738 A2 | 8/2007 |
| WO | WO2008091197 A1 | 7/2008 |
| WO | WO2009075625 A1 | 6/2009 |

OTHER PUBLICATIONS

Campbell, et al., A silicon-based 3-dimensional neural interface—Manufacturing process for an intracortical electrode array, IEEE Trans. Biomed. Eng., vol. 38, No. 8 (1991), 758.
Wise, et al., Microelectrodes, microelectronics, and implantable neural microsystems, Proc. IEEE, vol. 96, No. 7 (2008), 1184.

(Continued)

*Primary Examiner* — Lee S Cohen
(74) *Attorney, Agent, or Firm* — K. David Crockett, Esq.; Niky Economy Syrengelas, Esq.; Crockett & Crockett, PC

(57) ABSTRACT

A probe element and a method of forming a probe element are provided. The probe element includes a carrier comprising biodegradable and/or bioactive material; and at least one electrode coupled to the carrier.

11 Claims, 11 Drawing Sheets

(56) References Cited

OTHER PUBLICATIONS

Kewley, et al., Plasma-etched neural probes, Sens & Act., vol. 58, No. 1, (1997), 27.

Rousche, et al., Flexible polyimide-based intracortical electrode arrays with bioactive capability, IEEE Trans. Biomed. Eng., vol. 48, No. 3, (2001) 361.

Takeuchi, et al. Parylene flexible neural probes integrated with microfluidic channels, vol. 5, No. 5 (2005), 519.

Fernandez, et al., Study of functional viability of SU-8-based microneedles for neural applications, J Micromech. & Microeng., vol. 19, No. 2 (2009), 025007.

Lee, et al., Biocompatible benzocyclobutene (BCB)-based neural implants with microfluidic channel, vol. 20, 2004, 404.

Canham, et al., Silicon quantum wire array fabrication by electrochemical and chemical dissolution of wafers, Appl. Phys. Lett., vol. 57, (1990), 1046.

LT Canham, Bioactive silicon structure fabrication through nanoetching techniques, Adv. Matt.. vol. 7, No. 12 (1995), 1033.

Tasciotti, et al., Mesoporous silicon particles as a multistage delivery system for imaging and therapeutic applications, vol. 3 (2008), 151.

Park, et al., Biodegradable luminescent porous silicon nanoparticles for in vivo applications, Nature Materials, vol. 8, (2009), 331.

Feh, et al, Microfabricated microneedle with porous tip for drug delivery, J Microeng. & Micromach, vol. 16, (2006), 958.

Chen, et al., Silicon microneedle array with biodegradable tips for transdermal drug delivery, Microsyst Technol, vol. 14, (2008), 1015.

Persson, et al., Porous silicon as a neural electrode material, J. Biomater. Sci. Polymer Edn,, vol. 18, No. 19, (2007), 1301.

Moxon, et al., Bioactive properties of nanostructured porous silicon for enhancing electrode to neuron interfaces, J. Biomater. Sci. Polymer Edn, vol. 18, No. 10, (2007), 1263.

Moxon, et al., Nanostructured Surface Modification of Ceramic-Based Microelectrodes to Enhance Biocompatibility for a Direct Brain-Machine Interface, IEEE Trans. Biomed. Eng., vol. 51, No. 6, (2004), 881.

Johansson, et al., Porous silicon as a potential electrode material in a nerve repair setting: Tissue reactions, Acta Biomaterialia, vol. 5, (2009), 2230.

Rodriguez, et al., Fabrication of Silicon Oxide Microneedles from Macroporous Silicon, Sensors and Actuators B 109 (2005), 135-140.

Reed et al., Microsystems for Drug and Gene Delivery, Proceedings of the IEEE, vol. 92, No. 1, (2004), 56-75.

Ashraf et al., Design, Fabrication and Analysis of Silicon Hollow Microneedles for Transdermal Drug Delivery System for Treatment of Hemodynamic Dysfunctions, Cardiovasc Eng, vol. 10, (2010), 91-108.

\* cited by examiner

PROBE ELEMENT AND METHOD OF FORMING A PROBE ELEMENT

TECHNICAL FIELD

Various embodiments relate generally to a probe element and a method of forming a probe element.

BACKGROUND

Implantable electronic devices for neural recording and/or stimulation may include either insulated conductive microwires with exposed tips or micromachined neural probes with an array of microelectrodes. These devices are considered as an important neurotechnology for system neuroscience and neuroprosthetics. However, reactive tissue response to these devices deteriorates the device performance over time by compromising the recording stability, signal quality, and operating lifetime (their chronic or long-term performance). Thus, it is desirable to have probes designs which can suppress the reactive tissue response and/or reduce chronic tissue response.

The basic function of a neural probe is to introduce an array of microelectrodes into a neural tissue along with their electrical wiring. As the probe is physically inserted into the tissue, it is desirable that mechanical strength of the probe is greater than the force required to insert the probe into the tissue to prevent buckling or fracture of the probe. Moreover, during insertion, the probe may injure or destroy the tissue in a local area producing a "kill zone". It is preferred that the kill zone is minimal and the nerve cells near the microelectrodes are preserved for an effective chronic recording and stimulation. To limit the kill zone solely to the area intersected by the probe, the surrounding tissues should be subjected to negligible stretching or compression during the probe penetration. This can be possible if the probe cuts its way through injuring only the intersected structures and preventing propagation of the damage into the surrounding tissues. This may then minimize the kill zone. Otherwise, stretching or compression may tear the neural tissue which leads to neural cell death and/or rupturing of blood capillaries. Bleeding due to rupturing of blood capillaries can cause extensive neuronal displacement or destruction. Thus, it is desirable to have a probe designed such that the probe can be inserted into the tissue without distorting or tearing the walls.

Conventional neural probes exhibit either a conical shape with round cross-sectional profile (as in "Utah Probe" or glass micropipettes) or a blade shape with rectangular or semi-circular cross-sectional geometry (as in "Michigan Probe") [1], [2]. The conical shape may seem ideal for probe geometry since the sharp tip of the probe can create a tiny hole through which the probe can penetrate deeper into the tissue by gently pushing the adjacent tissue aside. This mechanism may work if the neural tissue were made of a homogenous elastically deformable material. However, the neural tissue is fibrous in nature being packed with myelinated axons, microtubules, and neurofilaments criss-crossing one another forming a "fishnet" like woven structure. A conical probe penetrating into the tissue would shear the tissue with the tissue elements eventually stretching and forming a fibrous band around the probe. With further penetration of the probe, the band becomes larger and tighter. Thus, additional force is required to cause the probe to penetrate further into the tissue. The additional force on the penetrating probe may spread to adjacent tissues as the band compacts. As such, the tissues adjacent to the band may be pulled in tension. When the tissue is pulled in tension beyond its elastic limits, membranes of neurons may rupture. Small blood vessels may also be torn and subsequent microhemorrhages may destroy or displace the neural tissue on a large scale. Thus, a conically shaped probe is probably unsuitable for atraumatic implant.

Blade type probes, depending on their microfabrication approach, may exhibit either a characteristic structure with thickness and width converging into a point-like sharp tip or a profile having a uniform thickness terminating at a sharp edge at the tip. In either geometry, the thickness of the blade type probe is considerably reduced as compared to its width. Thus, the blade type probe may ease the band of tight tissue that can tear as compared to the conically shaped probe. However, it is desirable to further reduce penetration trauma to the tissue and/or to prevent tearing of the tissue.

SUMMARY

According to one embodiment of the present invention, a probe element is provided. The probe element includes a carrier comprising biodegradable and/or bioactive material; at least one electrode coupled to the carrier.

In one embodiment, the at least one electrode includes at least one microelectrode. The at least one electrode may include a plurality of electrodes.

In one embodiment, the carrier includes a tapered portion, and the tapered portion includes biodegradable and/or bioactive material.

In one embodiment, the carrier includes a layer having a first surface and a second surface facing away from the first surface, and the tapered portion is disposed on the second surface of the layer.

In one embodiment, the layer includes at least a planar layer portion.

In one embodiment, the tapered portion includes a diminishing dimension in a direction perpendicular to and away from the second surface of the layer.

In one embodiment, the tapered portion extends along at least a part of a length of the layer, and the diminishing dimension of the tapered portion provides an edge along an axis parallel to and furthest away from the second surface of the layer.

In one embodiment, the biodegradable and/or bioactive material includes biodegradable and/or bioactive silicon. The biodegradable and/or bioactive material may include porous silicon.

In one embodiment, the layer includes two opposite sides converging to form a pointed tip.

In one embodiment, the layer includes at least one material selected from a group of materials consisting of parylene, polyimide, SU-8 and benzocyclobutene (BCB).

In one embodiment, the probe element further includes at least one electrical lead and/or an insulated wiring coupled to the at least one electrodes.

In one embodiment, the at least one electrode includes at least one material selected from a group of materials consisting of: titanium, platinum, iridium and n-doped silicon.

In one embodiment, the probe element further includes at least one fluidic channel.

According to one embodiment of the present invention, an implantable electronic device for neural recording and/or stimulation is provided. The implantable electronic device includes at least one probe element as described above.

According to one embodiment of the present invention, a method of forming a probe element is provided. The method includes forming at least two trenches in a carrier comprising biodegradable and/or bioactive material; isotropically etching material of the carrier beginning from the trenches such that the probe element is formed comprising a first surface and a tapered portion opposite to the first surface.

In one embodiment, the first surface includes a planar surface portion.

In one embodiment, the method further includes coupling at least one electrode to the first surface of the carrier.

In one embodiment, the biodegradable and/or bioactive material includes biodegradable and/or bioactive silicon. The biodegradable and/or bioactive material may include porous silicon.

In one embodiment, the method further includes depositing a mask film above the carrier; patterning the mask film to expose parts of the carrier; and etching the exposed parts of the carrier to form the trenches.

In one embodiment, the mask film includes tetraethyl orthosilicate.

In one embodiment, the tetraethyl orthosilicate film is deposited above the carrier by plasma enhanced deposition.

In one embodiment, the patterning of the mask film includes ultraviolet lithography and reactive ion etching.

In one embodiment, the patterning of the mask film includes forming a resist above the mask film, and the etching of the exposed parts of the carrier is carried out after carrying out stripping of the resist.

In one embodiment, the etching of the exposed parts of the carrier is carried out in a deep reactive ion etching system.

In one embodiment, the method further includes depositing plasma enhanced tetraethyl orthosilicate in the trenches; and etching the deposited plasma enhanced tetraethyl orthosilicate to remove the deposited plasma enhanced tetraethyl orthosilicate from the bottom of the trenches to expose areas of the carrier and to keep the deposited plasma enhanced tetraethyl orthosilicate on the sidewalls of the trenches.

In one embodiment, the deposited plasma enhanced tetraethyl orthosilicate is removed from the bottom of the trenches by a reactive ion etching oxide etch process.

In one embodiment, the method further includes etching the exposed areas of the carrier to form a desired shape for the probe element; and removing the deposited tetraethyl orthosilicate film from the etched carrier.

In one embodiment, the exposed areas of the carrier are etched by plasma etching in a deep reactive ion etching system.

In one embodiment, the deposited tetraethyl orthosilicate film is removed from the carrier by buffered oxide wet etching.

In one embodiment, the carrier is a silicon wafer.

In one embodiment, the method further includes converting the silicon wafer into a porous silicon structure by electrochemical anodization or stain etching.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DETAILED DESCRIPTION

Embodiments of a probe element and a method of forming a probe element will be described in detail below with reference to the accompanying figures. It will be appreciated that the embodiments described below can be modified in various aspects without changing the essence of the invention.

Figure 1A:
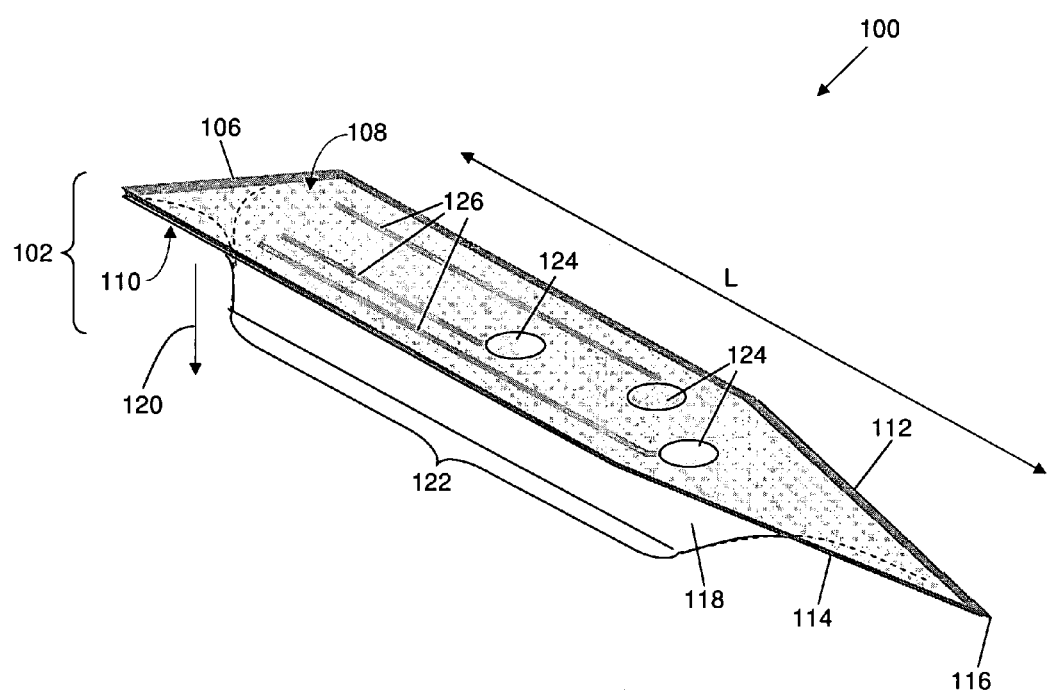
FIG. 1a shows a schematic three-dimensional top view of a probe element according to one embodiment of the present invention.
Figure 1B:
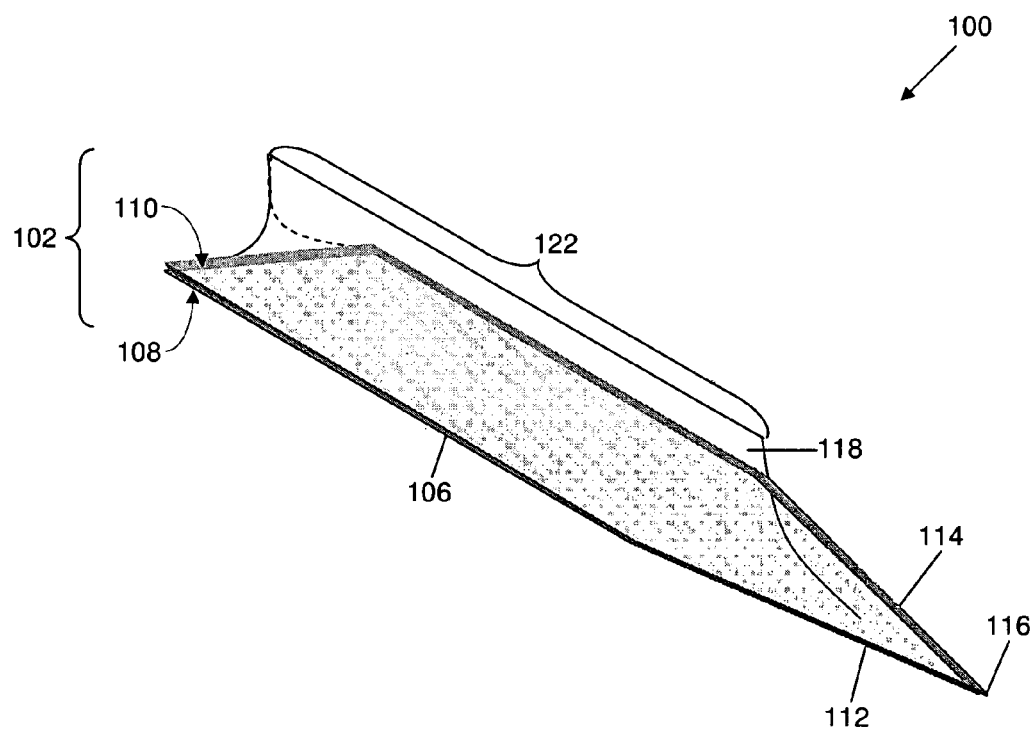
FIG. 1b shows a schematic three-dimensional bottom view of a probe element according to one embodiment of the present invention.
Figure 1C:
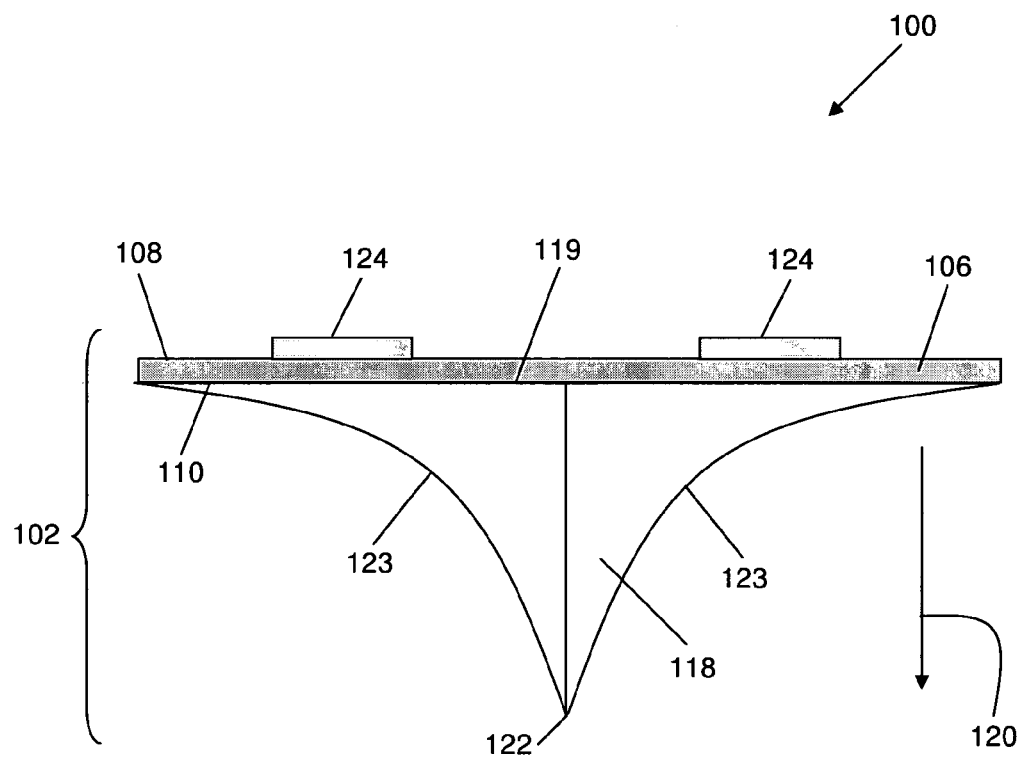
FIG. 1c shows a schematic cross-sectional view of a probe element according to one embodiment of the present invention.

FIG. 1a shows a schematic three-dimensional top view of a probe element 100. FIG. 1b shows a schematic three-dimensional bottom view of the probe element 100. FIG. 1c shows a schematic cross-sectional view of the probe element 100. The probe element 100 has a carrier 102. The carrier 102 may include biodegradable and/or bioactive material. The carrier 102 includes a layer 106 having a first surface 108 and a second surface 110 facing away from the first surface 108. In one embodiment, the layer 106 may be a planar layer portion of the carrier 102. Thus, the first surface 108 and the second surface 110 may be planar surfaces. The layer 106 has two opposite sides 112, 114 which are parallel to each other. The two opposite sides 112, 114 of the layer 106 gradually converge to form a pointed tip 116. The layer 106 may be made of different materials, e.g. biocompatible materials. Some examples of the material used for the layer 106 include parylene, polyimide, SU-8 and benzocyclobutene (BCB).

In one embodiment, the carrier 102 also includes a tapered portion 118. The tapered portion 118 is disposed on the second surface 110 of the layer 106. A surface 119 of the tapered portion 118 contacts the second surface 110 of the layer 106. The surface 119 of the tapered portion 118 may be planar. The tapered portion 118 extends along at least a part of a length (L) of the layer 106. That is, the length of the tapered portion 118 may be smaller than the length (L) of the layer 106. In one embodiment, the tapered portion 118 may extend along the whole length (L) of the layer 106. Further, the tapered portion 118 has a diminishing dimension in a direction (as indicated by arrow 120) perpendicular to and away from the second surface 110 of the layer 106. The diminishing dimension of the tapered portion 118 provides an edge 122 along an axis parallel to and furthest away from the second surface 110 of the layer 106. The tapered portion 118 has a deltoid cross-sectional profile as shown in FIG. 1c. The tapered portion 118 has the edge 122 (which is viewed as a tip from the cross-sectional view shown in FIG. 1c) and two curved side surfaces 123. The two side surfaces 123 are substantially concave. The edge 122 of the tapered portion 118 can facilitate the ease of the probe element 100 into a tissue (e.g. soft tissue such as brain and spinal cord), minimizing the trauma or bleeding due to dimpling of the tissue and capillaries.

Figure 1D:
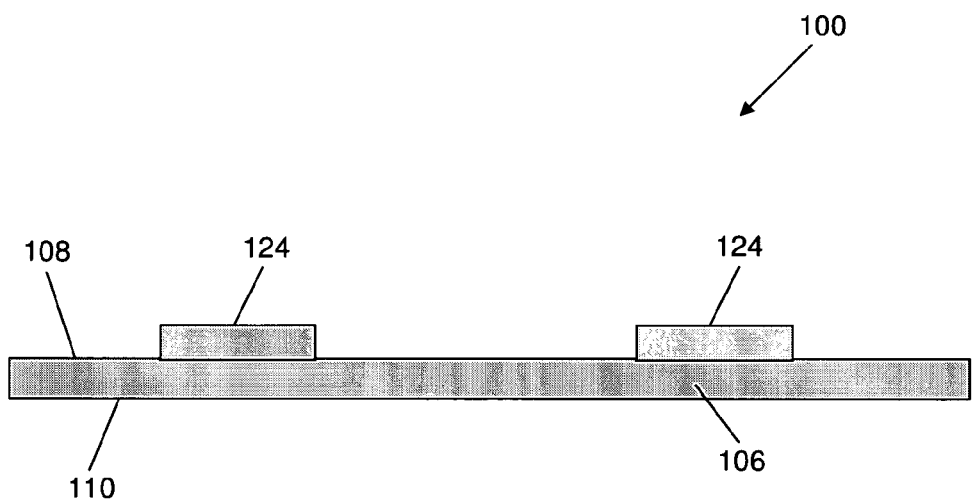
FIG. 1d shows a schematic cross-sectional view of a layer and electrodes of a probe element according to one embodiment of the present invention.

The tapered portion 118 may be used as a drug delivery platform. The tapered portion 118 may be made of biodegradable and/or bioactive material. In one embodiment, the biodegradable and/or bioactive material may be biodegradable and/or bioactive silicon. In another embodiment, the biodegradable and/or bioactive material may be porous silicon. Porous silicon fulfills the requirements of biodegradability and compatibility with microfabrication techniques. Further, porous silicon can be dissolved in the body within a short duration. After the porous silicon tapered portion 118 is dissolved in the body, the probe element 100 is as shown in FIG. 1d, leaving behind the layer 106 with electrodes 124 (which are described hereinafter). Biodegradation of the porous silicon tapered portion 118 can avoid complications due to mechanical impedance mismatch between the probe element 100 and the tissue.

In one embodiment, the probe element 100 also has at least one electrode 124 coupled to the carrier 102. In one embodiment, the probe element 100 may have a plurality of electrodes 124. For illustration purposes, three electrodes 124 are shown in FIG. 1a, and two electrodes 124 can be seen in FIGS. 1c and 1d. The electrode(s) 124 may be disposed on the layer 106 of the carrier 102, more specifically on the first surface 108 of the layer 106. Each electrode 124 may be a microelectrode. The probe element 100 may further include at least one electrical lead and/or an insulated wiring 126 coupled to the at least one electrode 124. The electrical lead(s) and/or insulated wiring(s) 126 may be embedded in the layer 106. Each electrode 124 may be coupled to a corresponding electrical lead and/or insulated wiring 126. The electrode(s) 124 and the electrical lead(s) and/or insulated wiring(s) 126 establish electrical communication with a tissue when the probe element 100 is inserted into a tissue.

Different materials may be used for manufacturing the electrode(s) 124. Some examples of the materials for the electrode(s) 124 may include titanium, platinum, iridium and n-doped silicon. Porous silicon may be a potential electrode material but it is necessary to first inhibit biodegradation of porous silicon by increasing its stability.

In one embodiment, the probe element 100 may further include at least one fluidic channel (not shown). The fluidic channel(s) may be used for injecting neurotrophic agents in the tissue to suppress reactive tissue response and facilitate neural growth. The fluidic channel(s) is an additional feature of the probe element 100, as the probe element 100 is still able to fulfill its function without the fluidic channel(s).

Figure 2:
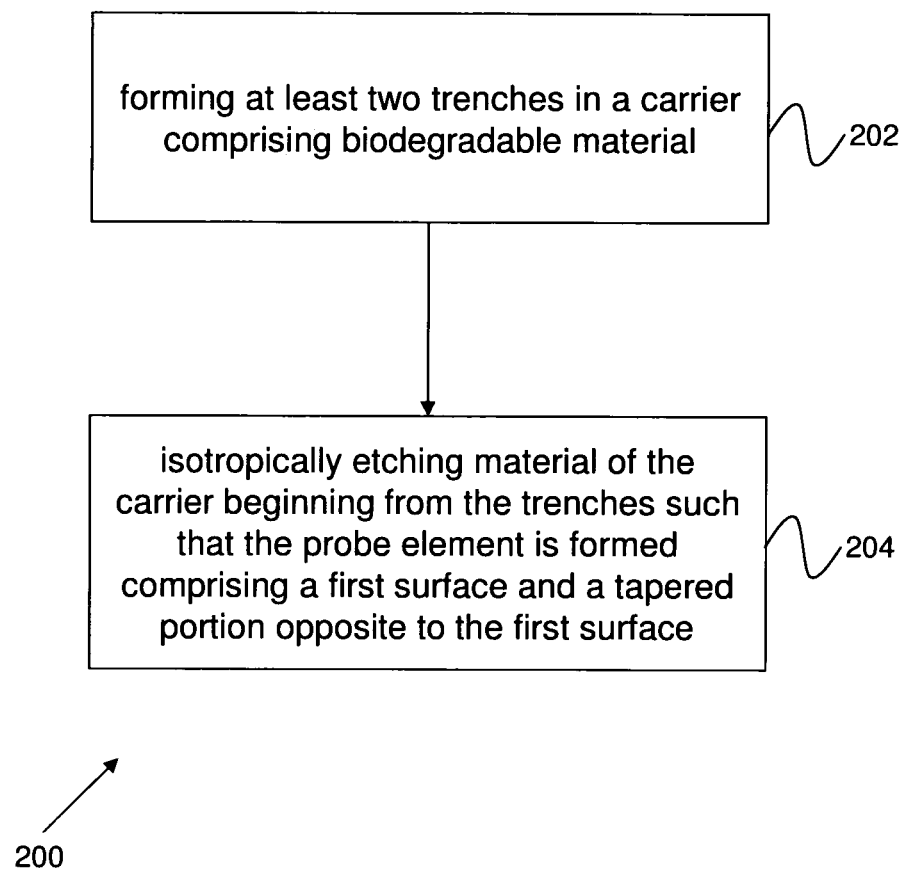
FIG. 2 shows a flowchart of a method of forming a probe element according to one embodiment of the present invention.

FIG. 2 shows a flowchart 200 of a method of forming a probe element. At 202, at least two trenches are formed in a carrier including biodegradable and/or bioactive material. At 204, material of the carrier is isotropically etched beginning from the trenches such that the probe element is formed including a first surface and a tapered portion opposite to the first surface.

Figure 3:
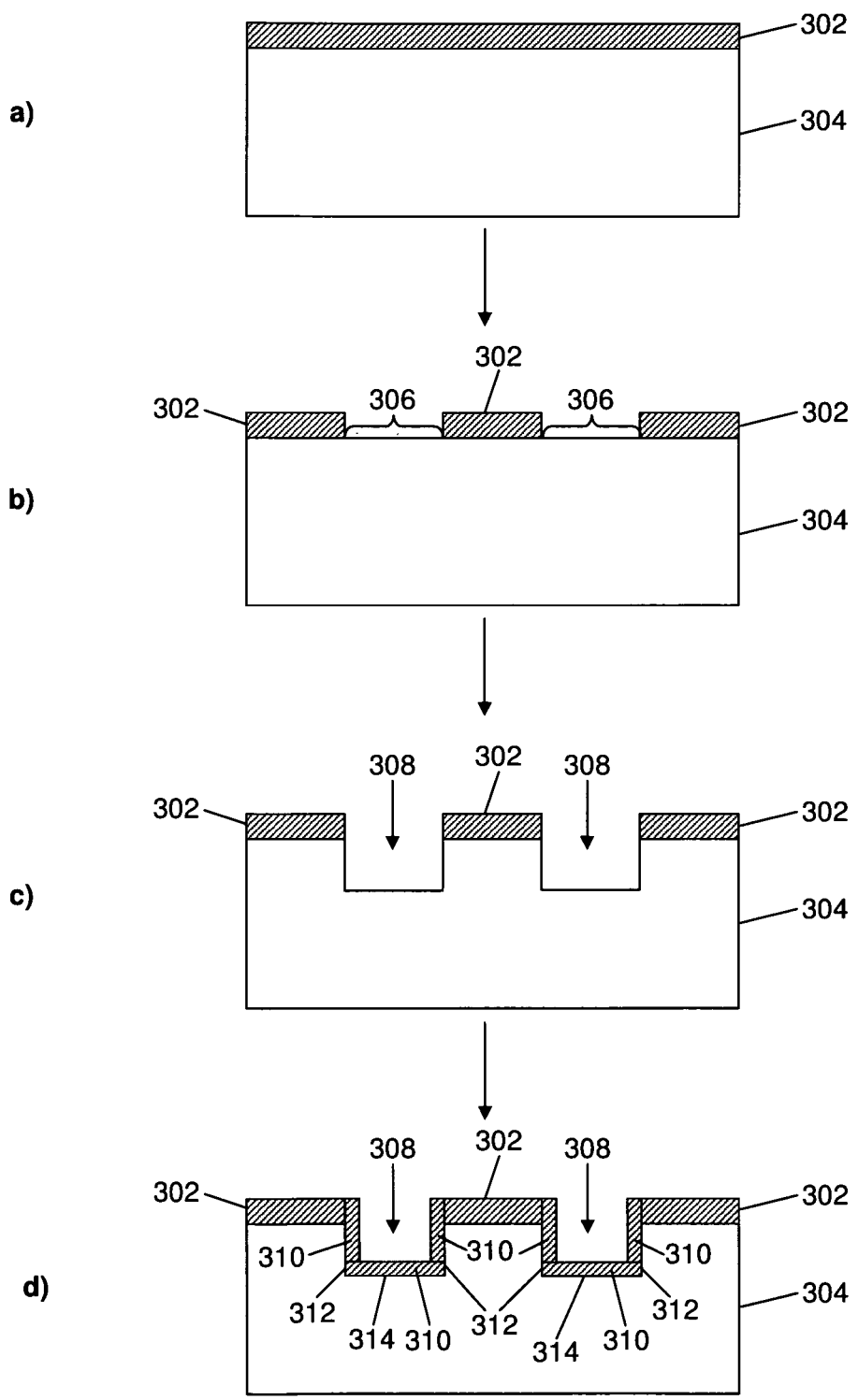
FIGS. 3a to 3g show a process of forming a probe element according to one embodiment of the present invention.
Figure 3:
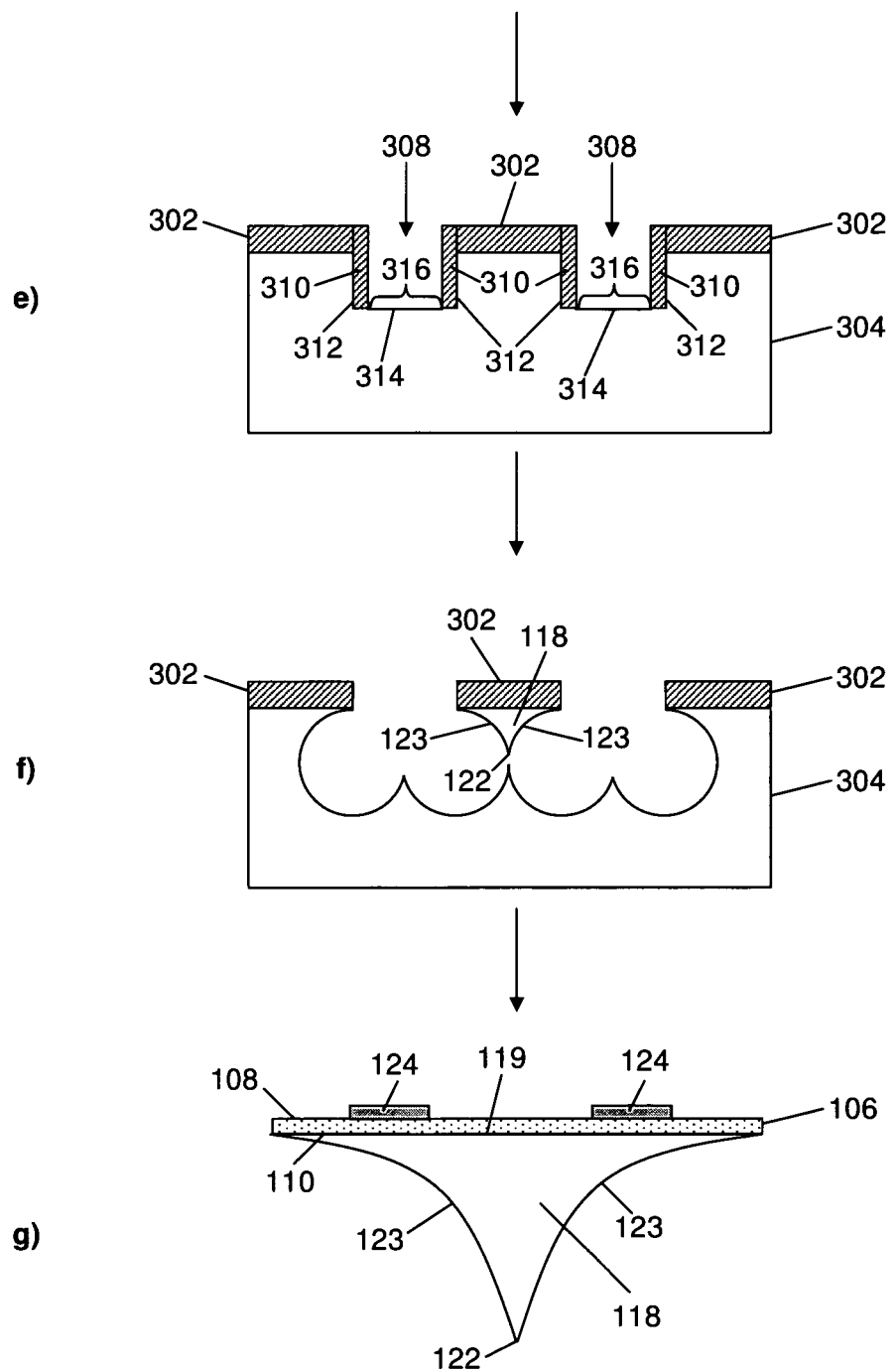

FIGS. 3a to 3g show a process of forming a probe element. FIG. 3a shows that a mask film 302 is deposited above a carrier 304. The mask film 302 is deposited above the carrier 304 by plasma enhanced deposition. The mask film 302 may include tetraethyl orthosilicate. The mask film 302 may have a thickness of about 0.5-2.0 μm. The carrier 304 may be a substrate or wafer 304. The carrier 304 may include biodegradable and/or bioactive material. In one embodiment, the biodegradable and/or bioactive material may be biodegradable and/or bioactive silicon. In another embodiment, the biodegradable and/or bioactive material may be porous silicon. The silicon material of the carrier 304 (substrate or wafer) may be converted into porous silicon before micromachining of the probe element 100 (at wafer scale). The silicon material of the carrier 304 may be converted into porous silicon by electrochemical anodization or stain etching.

FIG. 3b shows that the mask film 302 is patterned to expose parts 306 of the carrier 304. The exposed parts 306 of the carrier 304 may have a width of about 10-100 μm. The patterning of the mask film 302 is performed by ultraviolet lithography and reactive ion etching. For example, the mask film may be patterned in a reactive ion etching chamber after ultraviolet lithography. In one embodiment, the patterning of the mask film 302 may include forming a resist (not shown) above the mask film 302. If the resist is a positive resist, parts of the positive resist to be removed for patterning the mask film 302 are exposed to light. If the resist is a negative resist, parts of the negative resist to be removed for patterning the mask film 302 are not exposed to light.

FIG. 3c shows that the exposed parts 306 of the carrier 304 are etched to form trenches 308. At least two trenches 308 are formed in the carrier 304. For illustration purposes, only two trenches 308 are shown. However, more than two trenches 308 can be formed in the carrier 304. The trenches 308 may have a depth of about 40-140 μm. The etching of the exposed parts 306 of the carrier 304 is carried out after carrying out stripping of the resist. The etching of the exposed parts 306 of the carrier 304 is carried out in a deep reactive ion etching system.

FIG. 3d shows that plasma enhanced tetraethyl orthosilicate 310 is deposited in the trenches 308. The plasma enhanced tetraethyl orthosilicate 310 is deposited on sidewalls 312 and the bottom 314 of the trenches 308. The plasma enhanced tetraethyl orthosilicate 310 may have a thickness of about 5000-10000 Å.

FIG. 3e shows that the deposited plasma enhanced tetraethyl orthosilicate 310 is etched to remove the deposited plasma enhanced tetraethyl orthosilicate 310 from the bottom 314 of the trenches 308 to expose areas 316 of the carrier 304 and to keep the deposited plasma enhanced tetraethyl orthosilicate 310 on the sidewalls 312 of the trenches 308. The deposited plasma enhanced tetraethyl orthosilicate 310 may be removed from the bottom 314 of the trenches 308 by a reactive ion etching oxide etch process. The reactive ion etching oxide etch process may be carried out using trifluoromethane (CHF3), argon and tetrafluoromethane (CF4).

FIG. 3f shows that the exposed areas 316 of the carrier 304 are etched (e.g. isotropically etched) to form a desired shape for the tapered portion 118. The exposed areas 316 of the carrier 304 may be etched by plasma etching in a deep reactive ion etching system. For example, the exposed areas 316 of the carrier 304 may be etched by a timed sulfur hexafluoride (SF6) plasma etching in the deep reactive ion etching system. The tapered portion 118 may have a deltoid cross-sectional profile. The tapered portion 118 has an edge 122 (which is viewed as a tip from the cross-sectional view shown in FIG. 3f) and two curved side surfaces 123.

FIG. 3g shows that the mask film 302 (e.g. the deposited tetraethyl orthosilicate film) is removed from the etched carrier 304 e.g. by buffered oxide wet etching. A layer 106 having a first surface 108 and a second surface 110 may be disposed above the tapered portion 118 (e.g. on or above the surface 119 of the tapered portion 118). The surface 119 of the tapered portion 118 may be in contact with the second surface 110 of the layer 106. At least one electrode 124 (e.g. two electrodes 124) is coupled to a first surface 108 of the layer 106.

Alternatively, the silicon material of the tapered portion 118 may be converted into porous silicon after structuring the probe element 100 (at individual device scale). The silicon material of the tapered portion 118 may be converted into porous silicon by electrochemical anodization or stain etching.

Figure 4A:
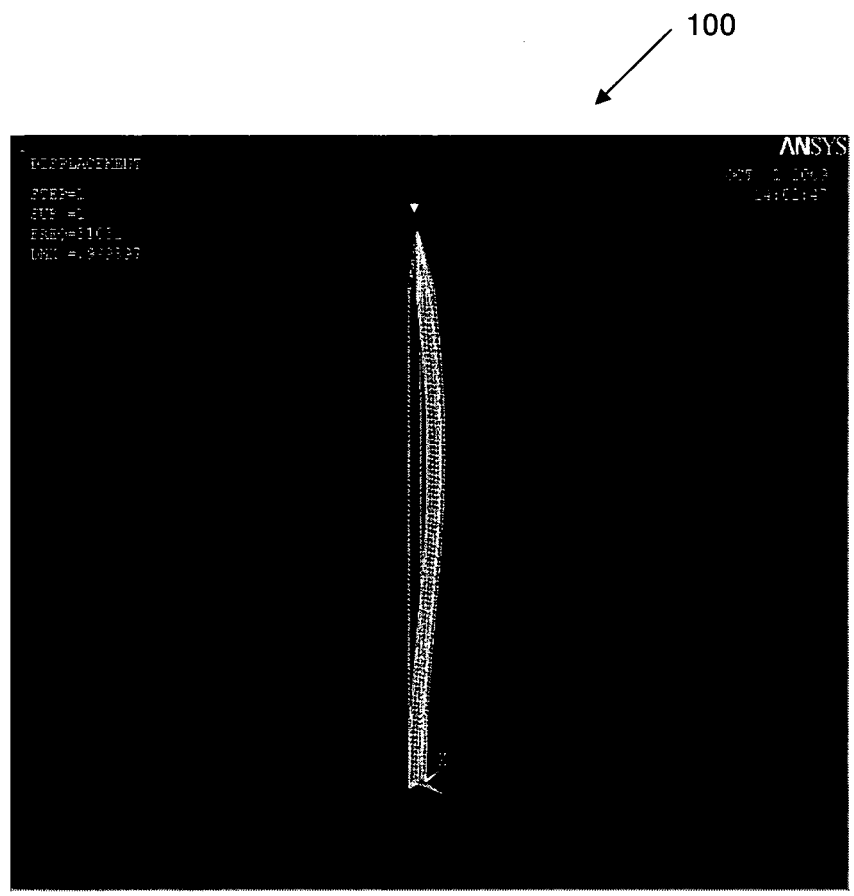
FIGS. 4a, 4b and 4c respectively show experimental results of a critical buckling load of a probe element of FIG. 1 and two conventional probes.
Figure 4B:
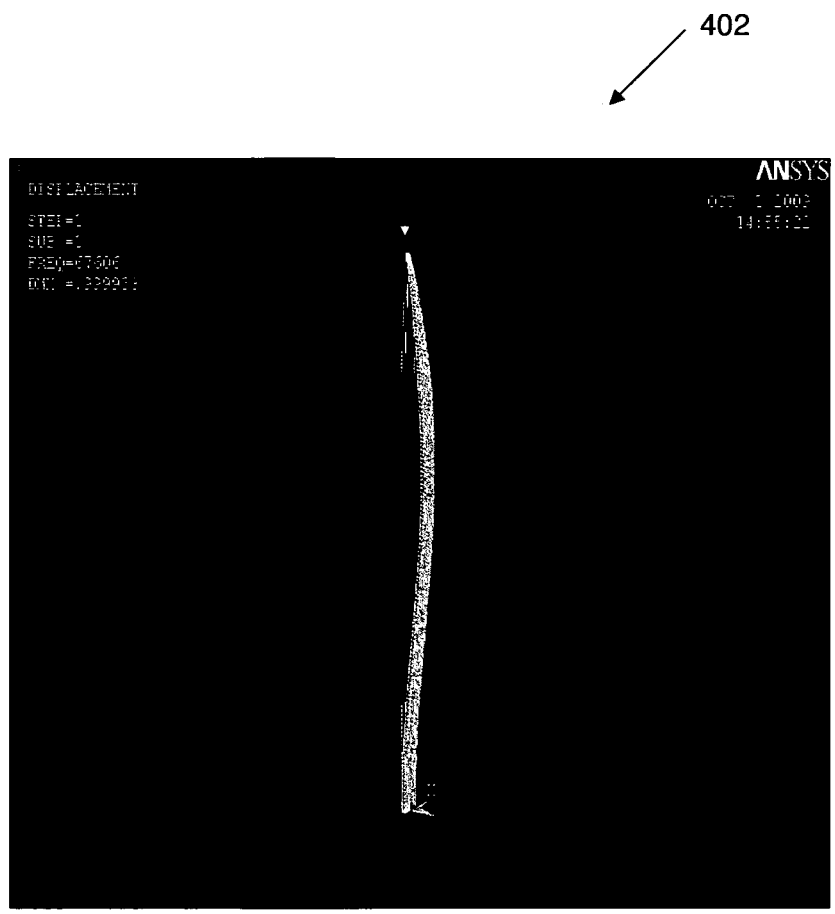
Figure 4C:
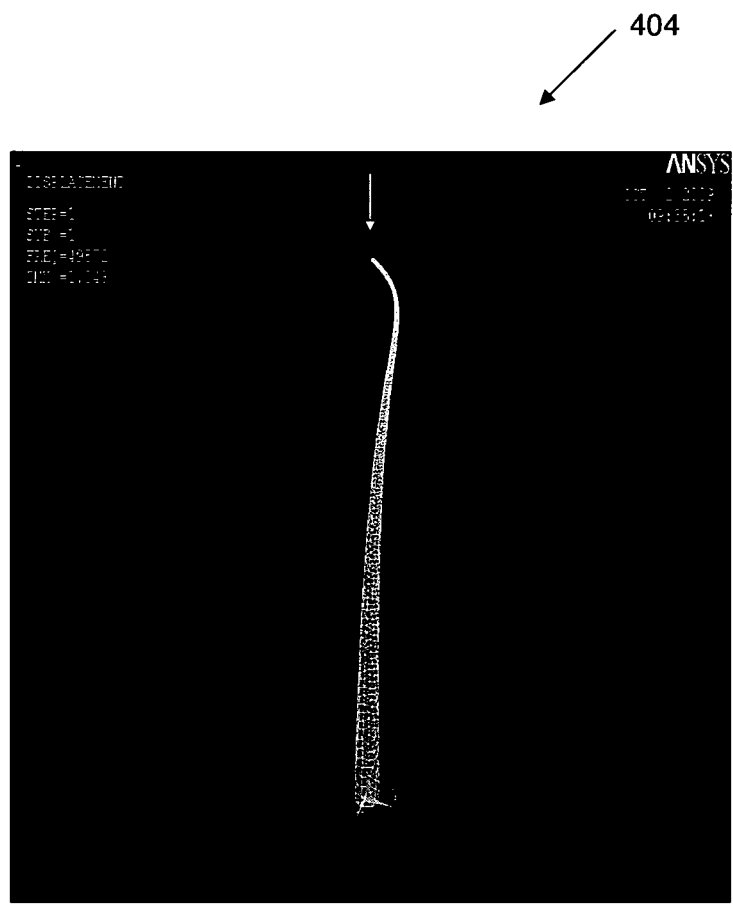

FIGS. 4a, 4b and 4c respectively show experimental results of a critical buckling load of the probe element 100 and two conventional probes 402, 404. The probe element 100 has a critical buckling load of about 32 mN. The first conventional probe 402 has a critical buckling load of about 68 mN. The second conventional probe 402 has a critical buckling load of about 50 mN.

The two conventional probes 402, 404 are stiffer than the probe element 100. However, the isotropically etched sharp tip and edges of the probe element 100 allow ease of insertion of the probe element 100 into a tissue. As such, the mechanical strength of the probe element 100 is greater than the force required to insert the probe element 100 into the tissue without buckling or fracturing of the probe element 100. Further, the tapered portion 118 of the probe element 100 may degrade within the tissue over time, leaving behind electrodes 124 on a layer 106 (e.g. biocompatible polymer layer). Biodegradation of the porous silicon tapered portion 118 can avoid complications due to mechanical impedance mismatch between the probe element 100 and the tissue. Unlike the probe element 100, the two conventional probes 402, 404 are not biodegradable and/or bioactive. Thus, the mechanical impedance mismatch of the two conventional probes 402, 404 with the tissue imposes an extra strain on the tissue, inflicting more damage. For chronic implants, the function of the conventional probes 402, 404 may fail as a scar tissue may encapsulate around the electrode(s) of the conventional probes 402, 404.

Figure 5:
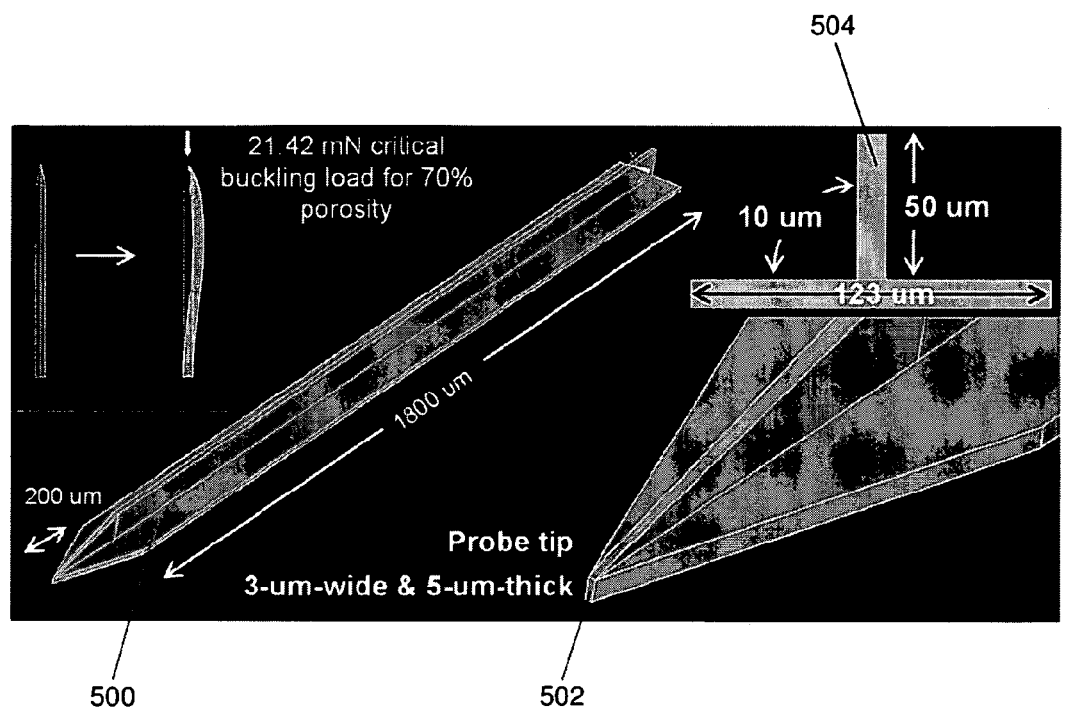
FIG. 5 shows schematic drawings of an exemplary probe element according to one embodiment of the present invention.

FIG. 5 shows schematic drawings of an exemplary probe element 500. The probe element 500 may have a length of about 2-4 mm, a width of about 50-200 μm, and a thickness of about 40-80 μm. The tip 502 of the probe element 500 may have a width of about 2-8 μm and a thickness of about 3-7 μm. In one embodiment, the probe element 500 may have a length of about 2 mm, a width of about 123 μm, and a thickness of about 60 μm. The tip 502 of the probe element 500 may have a width of about 3 μm and a thickness of about 5 μm. In other embodiments, the dimensions of the probe element and the tip of the probe element are different. Simulation is carried out for the exemplary probe element 500. A cantilever structure with a T-shape cross-sectional profile 504 which approximates the probe shape (e.g. deltoid) of the probe element 500 is used for the simulation. The simulation results show that the critical buckling load of the probe element 500 is greater than the minimum force required to advance the probe element 500 into a tissue.

If the probe element 500 is made of e.g. solid silicon, the probe element 500 can be advanced into the tissue without facing the problem of buckling since solid silicon is a highly stiff material with Young's modulus of about 200 GPa. If the silicon becomes porous, the stiffness of silicon is reduced and may be reduced proportionally with the porosity ratio. Porous silicon having a porosity ratio of about 70% has Young's modulus of about 12 GPa. If the probe element 500 is made of the above described porous silicon material, the simulation may generate a critical buckling load of about 21 mN for the probe element 500.

One or more of the above described probe element 100 may be used in an implantable electronic device for neural recording and/or stimulation for e.g. application of rehabilitation and neuroprothesis such as invasive brain-machine interface (BMI). The probe element 100 may be inserted into e.g. a brain tissue for neural recording and/or stimulation. The isotropically etched profile of the probe element 100 with ultrasharp tip and side edges allows the probe element 100 to transect the brain tissue across the full width and the full thickness of the brain tissue as the probe element 100 is advanced into the tissue. Thus, initial insult and penetration trauma to the brain tissue may be reduced. No or minimal tearing of the tissue may occur. The tissue encapsulation around the probe element 100, which may debilitate chronic functioning of the probe element 100, may be reduced.

However, given the stiffness of the probe material and the soft brain tissue undergoing constant micromotion, the cutting insult may continue to linger even after the probe element 100 is inserted. After a stab wound is inflicted by the probe element 100, the brain tissue can heal and completely recover from the wound within six months if the probe element 100 is removed right after the insertion. It would be difficult to identify the wound location if the stab was done under controlled, sterile conditions. On the other hand, for chronic implants, the brain tissue does not heal. Instead, the brain tissue may launch a reactive immunoresponse which forms a scar tissue around the probe. The scar tissue acts as an insulator further separating the electrode(s) 124 of the probe element 100 from neural cells. Thus, the performance of neural stimulation and recording of the probe element 100 may be degraded as the signals decay rapidly with the increased distance between the electrode(s) 124 and the neural cells. To reduce the formation of scar tissue, various materials that are more compliant such as biocompatible polymers including polyimide, parylene, SU-8, and benzocyclobutene (BCB) may be used for the probe element 100, in particularly the layer 106 of the probe element 100. Post-penetration insult to the tissue may be reduced by reducing mismatch between the mechanical impedances of the brain tissue and of the probe element 100. Nevertheless, the more compliant the probe element 100 becomes, the more difficult it gets to insert the probe element 100 into the tissue before reaching the critical load of buckling.

Further, a biodegradable and/or bioactive material may also be used for the probe element 100 (e.g. the tapered portion 118 of the probe element 100). Thus, the probe element 100 can be rendered to be biodegradable and/or bioactive postprocessing. Once the probe element 100 fulfills its function, i.e. to facilitate the insertion of an array of microelectrodes and their associated electrical wiring into the tissue, the tapered portion 118 of the probe element 100 is allowed to dissolve within the tissue leaving behind a compliant thin-film array of microelectrodes and their insulated metal tracing (as shown in FIG. 1d). Several biodegradable and/or bioactive materials can be used for the tapered portion 118 of the probe element 100. However, a material, which is also compatible with microfabrication procedure, is desirable.

For example, silicon, which is a raw material commonly used in microfabrication, is not biodegradable and/or bioactive. However, silicon becomes biodegradable and/or bioactive when it is made porous. Turning silicon into porous structure can be realized through e.g. electrochemical anodization or stain etching. The porosification technique can be applied either on the raw substrate (wafer-scale) before micromachining of the probe elements 100 or after structuring the probe elements 100 (individual device-scale). Therefore, porous silicon can be chosen as the material for the probe element 100 as it is biodegradable and/or bioactive and is compatible with microfabrication techniques.

Elemental silicon is an essential trace nutrient. Biodegradation product of porous silicon, orthosilicic acid ($Si(OH)_4$), is the form predominantly absorbed by humans and is naturally found in numerous tissues. Furthermore, silicic acid administered to humans is efficiently excreted from the body through the urine. Normal human blood plasma and serum contains silicon almost exclusively as monosilicic acid Si(OH), at below 1 mg/L corresponding to an average dietary intake of about 20-50 mg/day. The small thickness of the porous silicon tapered portion 118 of the probe element 100 may minimize the likelihood of toxic concentrations being reached. For example, the complete dissolution of a 10-by-10 probe array having about 2-mm-long, about 50-μm-thick microporous silicon probe elements 100 corresponds to an ingestion of less than about 1 mg, which is less than the bioavailable silicon found to be present in a pint of beer.

Further, the human body can dissolve porous silicon within a short duration. For example, SEM observations for a variety of porous silicon structures upon reacting with a simulated body fluid (SBF) indicated complete removal of mesoporous layers having about 1 μm thickness, about 70% porosity and about 640 m$^2$/g surface area within a day or so.

The rugged topography of porous silicon may be beneficial for the tissue compatibility of the probe element 100. The reactive tissue response that generates a capsule of connective tissue around the probe element 100 may be dependent on the surface topography of the probe element 100. For example, the capsule of connective tissue formed on solid silicon showed an increased thickness over time while the capsule of connective tissue formed on the porous silicon showed a constant and smaller thickness over time. Surface topography of about 1-2 μm of porous silicon may allow direct fibroblast attachment to the surface of the porous silicon and may produce a minimal connective tissue response. It may also prevent or diminish the presence of inflammatory cells at the interface between the probe element 100 and the tissue. If the pores of the porous silicon are larger than about 3.3 μm, inflammatory cells can invade the pores, i.e. infiltrate the surface of the porous silicon. Thus, the composition of the probe element 100 seems to be of secondary importance compared to the surface texture of the probe element 100. Nevertheless, the shape of the probe element 100 described above and its biodegradable and/or bioactive feature could address the soft tissue trauma and subsequent formation of connective-tissue capsule to the extent that the presence of electrodes 124 and their dielectric insulation for chronic implants would be of negligible concern.

While embodiments of the invention have been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

In this document, the following documents are cited:

[1] P K Campbell, K E Jones, R J Huber, K W Horch, and R A Normann, A silicon-based 3-dimensional neural interface—Manufacturing process for an intracortical electrode array, *IEEE Trans. Biomed. Eng.*, 1991, 38(8), 758

[2] K D Wise, A M Sodagar, Y Yao, M N Gulari, G E Perlin, and K Najafi, Microelectrodes, microelectronics, and implantable neural microsystems, Proc. IEEE, 2008, 96(7), 1184

What is claimed is:

1. A probe element, comprising:
    a carrier comprising:
        a layer having a first surface and a second surface facing away from the first surface;
        a tapered portion disposed on the second surface of the layer;
        at least one electrode coupled to the carrier;
    wherein the tapered portion comprises biodegradable and/or bioactive material;
    wherein the layer comprises at least one material selected from a group of materials consisting of parylene, polyimide, SU-8 and benzocyclobutene (BCB).

2. The probe element of claim 1, wherein the at least one electrode comprises at least one microelectrode.

3. The probe element of claim 1 wherein the at least one electrode comprises a plurality of electrodes.

4. The probe element of claim 1, wherein the layer comprises at least a planar layer portion.

5. The probe element of claim 1, wherein the tapered portion comprises a diminishing dimension in a direction perpendicular to and away from the second surface of the layer.

6. The probe element of claim 5, wherein the tapered portion extends along at least a part of a length of the layer, and wherein the diminishing dimension of the tapered portion provides an edge along an axis parallel to and furthest away from the second surface of the layer.

7. The probe element of claim 1, wherein the biodegradable and/or bioactive material comprises biodegradable and/or bioactive silicon.

8. The probe element of claim 7, wherein the biodegradable and/or bioactive material comprises porous silicon.

9. The probe element of claim 1, wherein the layer comprises two opposite sides converging to form a pointed tip.

10. The probe element of claim 1, further comprising at least one electrical lead and/or an insulated wiring coupled to the at least one electrode.

11. An implantable electronic device for neural recording and/or stimulation, comprising:
    at least one probe element comprising:
    a carrier comprising:
        a layer having a first surface and a second surface facing away from the first surface;
        a tapered portion disposed on the second surface of the layer;
        at least one electrode coupled to the carrier;
    wherein the tapered portion comprises biodegradable and/or bioactive material;
    wherein the layer comprises at least one material selected from a group of materials consisting of parylene, polyimide, SU-8 and benzocyclobutene (BCB).

* * * * *